(12) United States Patent
McCawley et al.

(10) Patent No.: US 10,610,351 B2
(45) Date of Patent: Apr. 7, 2020

(54) GAS CANISTERS AND METHODS FOR MAKING THEM

(71) Applicant: ALTAVIZ, LLC, Irvine, CA (US)

(72) Inventors: Matthew McCawley, San Clemente, CA (US); Matthew Flowers, Aliso Viejo, CA (US); Peter L. Bliss, Prior Lake, MN (US); Jack R. Auld, Laguna Niguel, CA (US)

(73) Assignee: PICOCYL, Golden, CO (US)

( * ) Notice: Subject to any disclaimer, the term of this patent is extended or adjusted under 35 U.S.C. 154(b) by 569 days.

(21) Appl. No.: 15/064,464

(22) Filed: Mar. 8, 2016

(65) Prior Publication Data
US 2017/0258583 A1    Sep. 14, 2017

(51) Int. Cl.
*A61F 2/16*    (2006.01)
*F17C 13/04*    (2006.01)
(Continued)

(52) U.S. Cl.
CPC .............. *A61F 2/1678* (2013.01); *A61F 2/14* (2013.01); *A61F 2/148* (2013.01); *A61F 2/167* (2013.01); *A61M 5/2053* (2013.01); *F17C 1/00* (2013.01); *F17C 13/04* (2013.01); *A61B 17/00* (2013.01); *A61B 2017/00526* (2013.01); *A61B 2017/00548* (2013.01); *A61F 2/1662* (2013.01); *A61M 11/02* (2013.01); *B65B 31/003* (2013.01); *F17C 2201/0109* (2013.01); *F17C 2201/058* (2013.01); *F17C 2203/0617* (2013.01); *F17C 2203/0643* (2013.01); *F17C 2205/032* (2013.01); *F17C 2209/221* (2013.01);
(Continued)

(58) Field of Classification Search
CPC ... A61F 2/1662; B60R 21/268; B60R 21/274; B65D 2543/00546; B65D 2543/00694; B65D 2543/00805; B65D 43/021; F17C 1/00; F17C 13/02; F17C 13/06; F17C 2201/0109; Y10T 137/1729; Y10T 137/1767
USPC .......... 215/355; 131/336; 220/581–582, 784, 220/787, 789, 802–804
See application file for complete search history.

(56) References Cited

U.S. PATENT DOCUMENTS 2,605,763 A * 8/1952 Smoot .................... A61M 5/30
141/19
2,613,849 A * 10/1952 Ward .................... A62C 13/70
222/5

(Continued)

FOREIGN PATENT DOCUMENTS

EP    1800972 B1    10/2008
GB    525714    9/1940

OTHER PUBLICATIONS

European Patent Office, International Search Report for corresponding International Application No. PCT/US2017/021446, dated Dec. 18, 2017, 7 pages.

(Continued)

*Primary Examiner* — Ernesto A Grano
(74) *Attorney, Agent, or Firm* — William A. English; Vista IP Law Group LLP (57) ABSTRACT

Canisters are provided that include a cylindrical body and a cap welded to the body to define a cavity filled with carbon dioxide or other fluid. The canisters may be loaded into a medical device, e.g., to provide an energy source for operating the device. Methods for making such canisters are also provided.

16 Claims, 9 Drawing Sheets

(51) Int. Cl.
    *A61B 17/00*     (2006.01)
    *A61F 2/14*     (2006.01)
    *F17C 1/00*     (2006.01)
    *A61M 5/20*     (2006.01)
    *B65B 31/00*     (2006.01)
    *A61M 11/02*     (2006.01)

(52) U.S. Cl.
    CPC .................. *F17C 2221/013* (2013.01); *F17C 2223/0123* (2013.01); *F17C 2223/0153* (2013.01); *F17C 2270/02* (2013.01); *F17C 2270/0736* (2013.01)

(56) References Cited

U.S. PATENT DOCUMENTS

| | | | | |
|---|---|---|---|---|
| 2,685,383 | A | | 8/1954 | Kochner |
| 3,156,369 | A | * | 11/1964 | Bowes .................. B65D 51/285 206/222 |
| 4,189,068 | A | | 2/1980 | Apellaniz |
| 4,954,149 | A | | 9/1990 | Fullemann |
| 5,029,730 | A | * | 7/1991 | Kostecki .................. F17C 5/06 137/223 |
| 5,957,898 | A | * | 9/1999 | Jepson .................. A61M 39/045 128/912 |
| 6,148,996 | A | * | 11/2000 | Morini .................. B65D 51/285 206/222 |
| 7,156,257 | B2 | | 1/2007 | de la Serna |
| 7,401,808 | B2 | | 7/2008 | Rossbach et al. |
| 8,215,481 | B1 | * | 7/2012 | Knickerbocker .... B65D 51/285 206/219 |
| 9,738,245 | B1 | * | 8/2017 | Stevens .................. B60R 21/274 |
| 2002/0007149 | A1 | | 1/2002 | Nelson et al. |
| 2008/0078769 | A1 | * | 4/2008 | Crunkleton, III .... B67D 1/0021 220/560.04 |
| 2009/0090741 | A1 | | 4/2009 | Oberhofer et al. |
| 2013/0025600 | A1 | | 1/2013 | Levy et al. |
| 2013/0317478 | A1 | | 11/2013 | Auld et al. |
| 2015/0282928 | A1 | | 10/2015 | Auld et al. |
| 2015/0329341 | A1 | | 11/2015 | Wilder et al. |
| 2016/0025269 | A1 | * | 1/2016 | Quail ........................ F17C 1/00 141/4 |
| 2017/0119522 | A1 | * | 5/2017 | Auld ..................... A61F 2/1672 |

OTHER PUBLICATIONS

European Patent Office, Written Opinion for corresponding International Application No. PCT/US2017/021446, dated Dec. 18, 2017, 9 pages.

* cited by examiner

GAS CANISTERS AND METHODS FOR MAKING THEM

TECHNICAL FIELD

The present disclosure relates generally to canisters for storing gases, and, more particularly, to single-use gas canisters that may be loaded into a medical device for providing energy during use of the medical device, and to methods for making such canisters.

BACKGROUND

Various surgical procedures involve the use of medical devices that require an energy source, e.g., to provide a discharge force to components of the devices. For example, an intraocular lens inserter device may be used to deliver a replacement lens within an eye suffering from a cataract. Such an IOL inserter may require an external power source to push a lens loaded into the inserter into a patient's eye.

Accordingly, energy sources for IOL inserters and other medical devices would be useful.

SUMMARY

The present disclosure is directed to canisters for storing gases, and, more particularly, to single-use gas canisters that may be loaded into a medical device for providing energy during use of the medical device, and to methods for making such canisters.

In accordance with an exemplary embodiment, a canister is provided that includes a cylindrical body and a cap attached to the body to define a cavity filled with gas, e.g., carbon dioxide. In some embodiments, the body includes a barrel region defining a first diameter, an enclosed first end, and a neck region defining a second diameter smaller than the first diameter and extending from the barrel region to an open second end defining an end wall, the body defining a central axis extending between the first end and the second end. The cap may include an annular portion including a closed first end an open second end, a penetrable or separable septum formed in the first end, and an annular flange extending radially from the second end of the annular portion, thereby defining a lower surface defining a plane substantially perpendicular to the central axis, and an annular projection extending from the lower surface.

In an exemplary embodiment, the first end of the annular portion may be inserted into the open second end of the body of the canister such that the annular portion is spaced from an interior surface of the neck region and the septum is disposed within the neck region, and the projection may be welded to the end wall of the second end of the body, thereby enclosing the cavity.

In accordance with another embodiment, a method is provided for making a canister that includes providing a cylindrical body comprising a barrel region defining a first diameter, an enclosed first end, and a neck region defining a second diameter smaller than the first diameter and extending from the barrel region to an open second end defining an annular end wall, the body defining a central axis extending between the first end and the second end; and providing a cap comprising an annular portion including a closed first end and an open second end, a penetrable or separable septum formed in the first end, and an annular flange extending radially from the second end of the annular portion, thereby defining a lower surface defining a plane substantially perpendicular to the central axis, and an annular projection extending from the lower surface. The first end of the annular portion may be inserted into the open second end of the body of the canister such that the annular portion is spaced from an interior surface of the neck region and the septum is disposed within the neck region. Gas, e.g., carbon dioxide, nitrogen, or hydrofluorocarbon, may be introduced into an interior of the body, and the projection may be welded to the end wall of the second end of the body, thereby enclosing a cavity of the canister with the gas therein.

In accordance with yet another embodiment, a method is provided for preparing a medical device for a procedure that includes providing a medical device comprising a housing including a chamber with a canister therein, an actuator, and a carriage in a first position within the housing, the canister comprising a cylindrical body comprising an enclosed first end and an open second end, a cap welded to the open second end including a septum, thereby defining an interior cavity filled with pressurized gas; and actuating the actuator to cause the carriage to move from the first position to a second position such that a pin on the carriage opens the septum, thereby releasing pressurized gas from the canister into one or more passages within the medical device. In one embodiment, the septum may be a relatively thin-walled panel that may be penetrated or punctured by the pin to open the cap. In another embodiment, the septum may include a relatively thin perimeter surrounding a relatively thick central portion such that, the pin causes at least a portion of the perimeter to tear otherwise separate to open the cap.

In accordance with still another embodiment, a method is provided for preparing a medical device for a procedure that includes providing a canister comprising a cylindrical body comprising an enclosed first end and an open second end, a cap welded to the open second end including a septum, thereby defining an interior cavity filled with pressurized gas; loading the canister into a housing of a medical device; and actuating the medical device to cause a pin in the housing to open the septum, thereby releasing pressurized gas from the canister into one or more passages within the medical device.

In accordance with another embodiment, a method is provided for performing a procedure that includes providing a medical device comprising a housing including a chamber with a canister therein, an actuator, and a carriage in a first position within the housing, the canister comprising a cylindrical body comprising an enclosed first end and an open second end, a cap welded to the open second end including a septum, thereby defining an interior cavity filled with pressurized gas; initially actuating the actuator to cause the carriage to move from the first position to a second position such that a pin on the carriage opens the septum, thereby releasing pressurized gas from the canister into one or more passages within the medical device to pressurize an incompressible liquid within the housing; and subsequently actuating the actuator, thereby causing the incompressible liquid to flow and deliver one of an agent and an implant from the medical device into a patient.

In accordance with still another embodiment, a medical device is provided that includes a housing comprising a treatment portion and an actuator portion including a chamber; a canister within the chamber comprising a cylindrical body comprising an enclosed first end and an open second end, a cap welded to the open second end and including a penetrable or separable septum, thereby defining an interior cavity filled with pressurized gas; a carriage movable within the housing from the first position, the carriage comprising a pin disposed adjacent the septum; and an actuator on the actuator portion coupled to the carriage such that initial activation of the actuator causes carriage to move from the first position to a second position such that the pin opens the septum, thereby releasing pressurized gas from the canister into one or more passages within the medical device.

Other aspects and features including the need for and use of the present disclosure will become apparent from consideration of the following description taken in conjunction with the accompanying drawings.

BRIEF DESCRIPTION OF THE DRAWINGS

It will be appreciated that the exemplary apparatus and components thereof shown in the drawings are not necessarily drawn to scale, with emphasis instead being placed on illustrating the various aspects and features of the illustrated embodiments. The drawings illustrate exemplary embodiments, in which.

DETAILED DESCRIPTION OF THE EXEMPLARY EMBODIMENTS

Figure 1A:
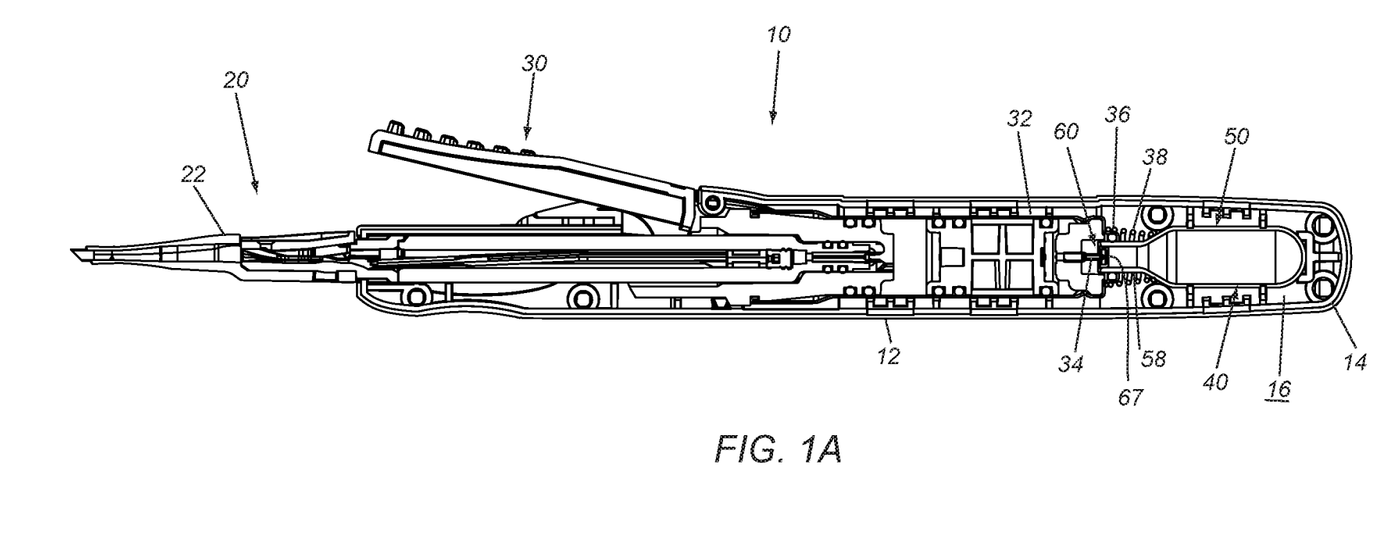
FIG. 1A is a cross-sectional view of an exemplary embodiment of an intraocular lens inserter including a single-use gas canister loaded therein.
Figure 1B:
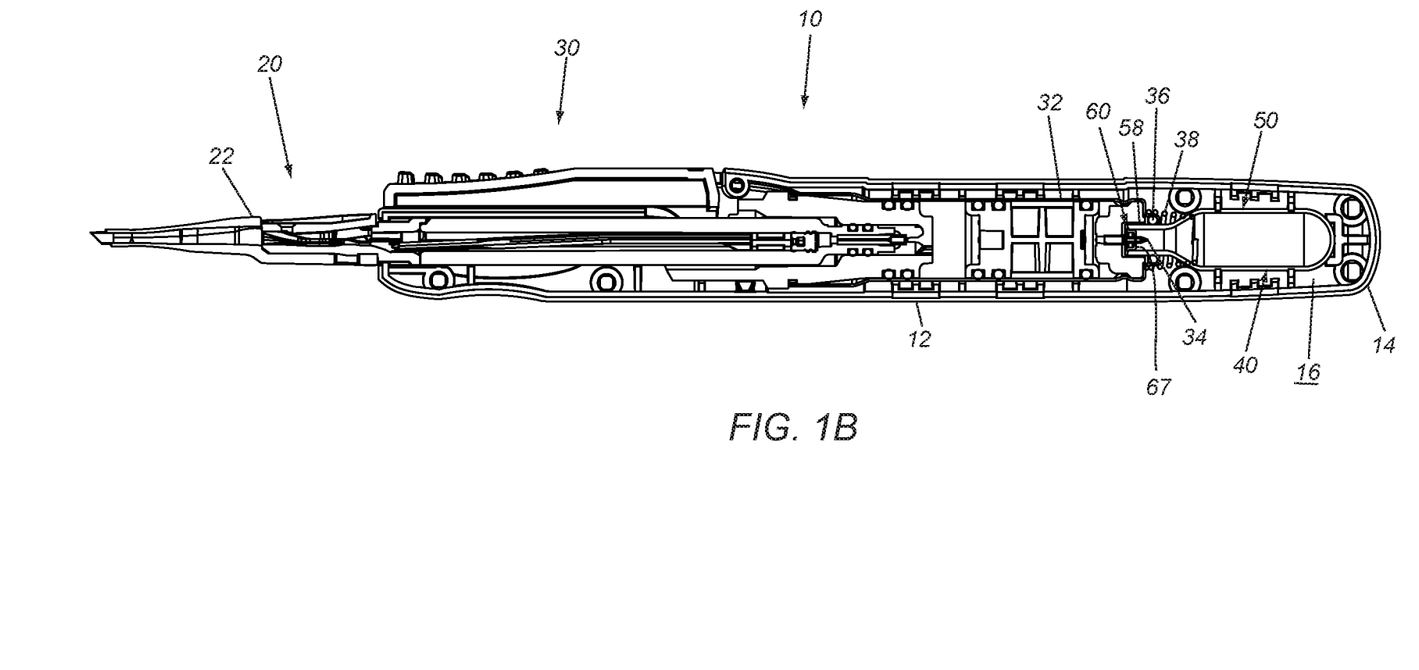
FIG. 1B is a cross-sectional view of the lens inserter of FIG. 1A with an actuator activated such that a pin punctures a septum of the gas canister to deliver gas therefrom for providing an energy source for the lens inserter.

Turning to the drawings, FIGS. 1A and 1B show an exemplary embodiment of intraocular lens (IOL) inserter 10 that includes a lens delivery portion 20, an actuator 30, and an energy device, e.g., canister 40. The intraocular lens inserter 10 may include a main body portion 12, which includes various cavities, recesses, and conduits, e.g., for providing communication between the canister 40 and the lens delivery portion 20, e.g., for delivering a lens (not shown) from a lens compartment 22 loaded into or onto, secured to, or otherwise forming a part of the lens delivery portion 20, e.g., as described in U.S. Publication No. 2015/0282928, the entire disclosure of which is expressly incorporated by reference herein.

For example, in an exemplary embodiment, the IOL inserter 10 may be provided with a canister 40 already provided within the housing 12, i.e., secured within chamber 16. Alternatively, the housing 12 may include a removable cap 14 allowing the canister 40 to be removed and replaced with a new canister, if desired. In the embodiment shown, the IOL inserter 10 includes a carriage 32 coupled to the actuator 30 and carrying a pin 34. When the canister 40 is loaded into the chamber 16 (e.g., during manufacturing or before use, such as, for example, where the canister 40 may be loaded into the housing 12 via the cap 14 sometime prior to use), the pin 34 may be disposed adjacent a septum 67 of the canister 40, as shown in FIG. 1A. In addition, the IOL inserter 10 may include an O-ring or other seal 36 disposed within the chamber 16 adjacent the pin 34, which may slidably engage a neck 58 of the canister 40, e.g., to provide a substantially fluid-tight seal between the neck 58 and the fluid passages within the IOL inserter 10.

Figure 1C:
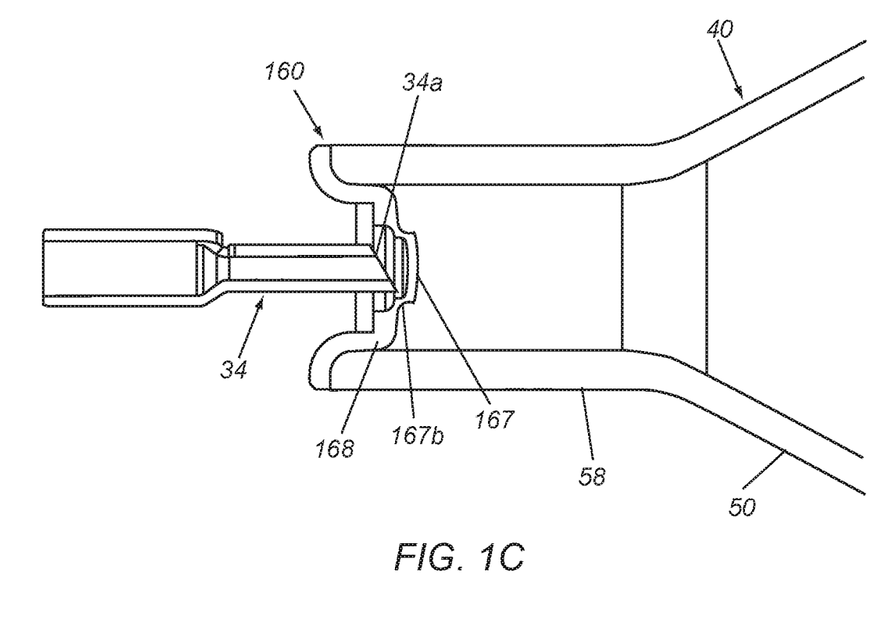
FIG. 1C is a detail showing an exemplary embodiment of a pin on an actuator, such as that shown in FIGS. 1A and 1B, which may be used to puncture the septum of a gas canister, such as that shown in FIGS. 5A and 5B.

Optionally, the carriage 32 may be slidably disposed within the main body portion 12, e.g., such that activation of the actuator 30, as shown in FIG. 1B, causes the carriage 32 and pin 34 to move axially, e.g., from the original or distal position shown in FIG. 1A proximally towards the canister 40 to the proximal position shown in FIG. 1B, thereby puncturing the septum 67 with the pin 34 and allowing gas to escape from the canister 40. Optionally, a spring or other biasing mechanism 38 may be provided within the main body portion 12, e.g., within the chamber 16 adjacent the O-ring 36 and/or around the neck 58 of the canister 40, for biasing the carriage 32 distally towards the distal position. Thus, when the actuator 30 is released, the carriage 32 may automatically return to the distal position and the pin 34 may be withdrawn from the septum 67, as shown in FIG. 1A. For example, FIG. 1C shows a pin 34 that may be coupled to the actuator 30 to press the septum 167 shown in FIGS. 5A and 5C inwardly to cause the perimeter 167b to at tear or otherwise separate at least partially between the central region 167a and the shoulder to open the canister 40.

In some instances, the lens compartment 22 may be a lens cartridge that may be loaded into the lens delivery portion 20. In other instances, the lens compartment 22 may be fixedly attached to or form an integral part of the IOL inserter 10. The IOL inserter 10 may be used to deliver a lens contained within the lens compartment 22 into a patient's eye. For example, the actuator 30 may be activated to deliver gas from the canister 40 through one or more passages of the main body portion 12, e.g., to pressurize an incompressible fluid to deliver the lens from the lens delivery portion 20 during a cataract surgical procedure.

Figure 2:
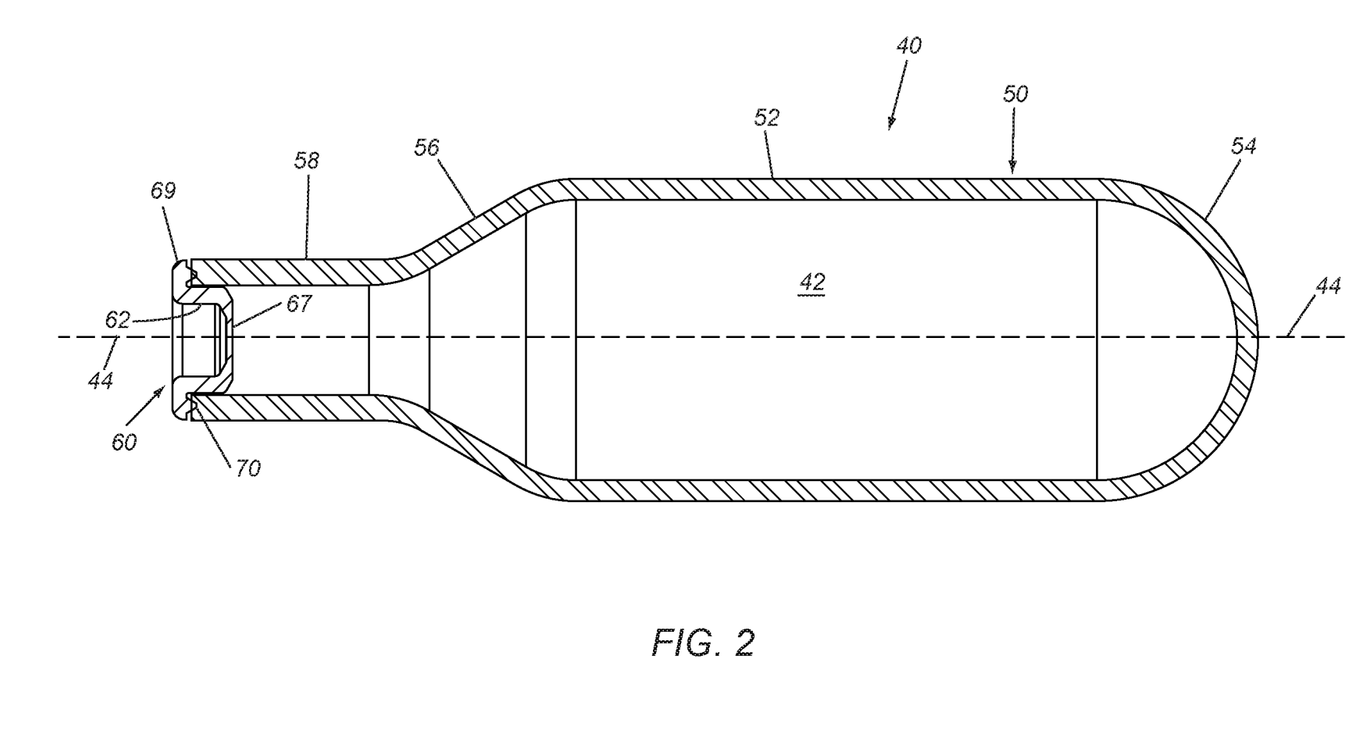
FIG. 2 is a cross-sectional view of an exemplary embodiment of a gas canister including a cap welded to a body.

Turning to FIG. 2, an exemplary embodiment of a canister 40 is shown. In some instances, the canister 40 may provide a single-use energy source for a medical device, such as the IOL inserter 10 of FIGS. 1A and 1B. Generally, the canister 40 includes a body 50 and a cap 60 welded to the body 50 to provide an enclosed cavity 42 filled with a fluid, e.g., carbon dioxide. The fluid contained within the enclosed cavity 42 may be used to provide a desired potential energy or discharge force to the IOL inserter 10, e.g., to advance the lens from the lens delivery portion 20. In alternative embodiments, the canister 40 may be filled with other two-phase gases, such as a hydrofluorocarbon (e.g., HFC-134a), or a single-phase gas, such as nitrogen. The volume of the cavity 42 may be sufficient to provide energy to the medical device, e.g., a discharge force for the IOL inserter 10 that may be substantially constant and/or controlled when the actuator 30 is actuated. In an exemplary embodiment, the cavity 42 may have an interior volume of no more than about 1.8 milliliters (1.8 mL), or not more than about one milliliter (1 mL), e.g., between about 0.5-1.8 mL, or between about 0.68-0.75 mL. However, in other embodiments, the interior volume of the cavity 42 may be any desired volume. For example, in some instances, the interior volume of the cavity 42 may be greater than 1.8 mL or less than 0.5 mL.

Figure 3:
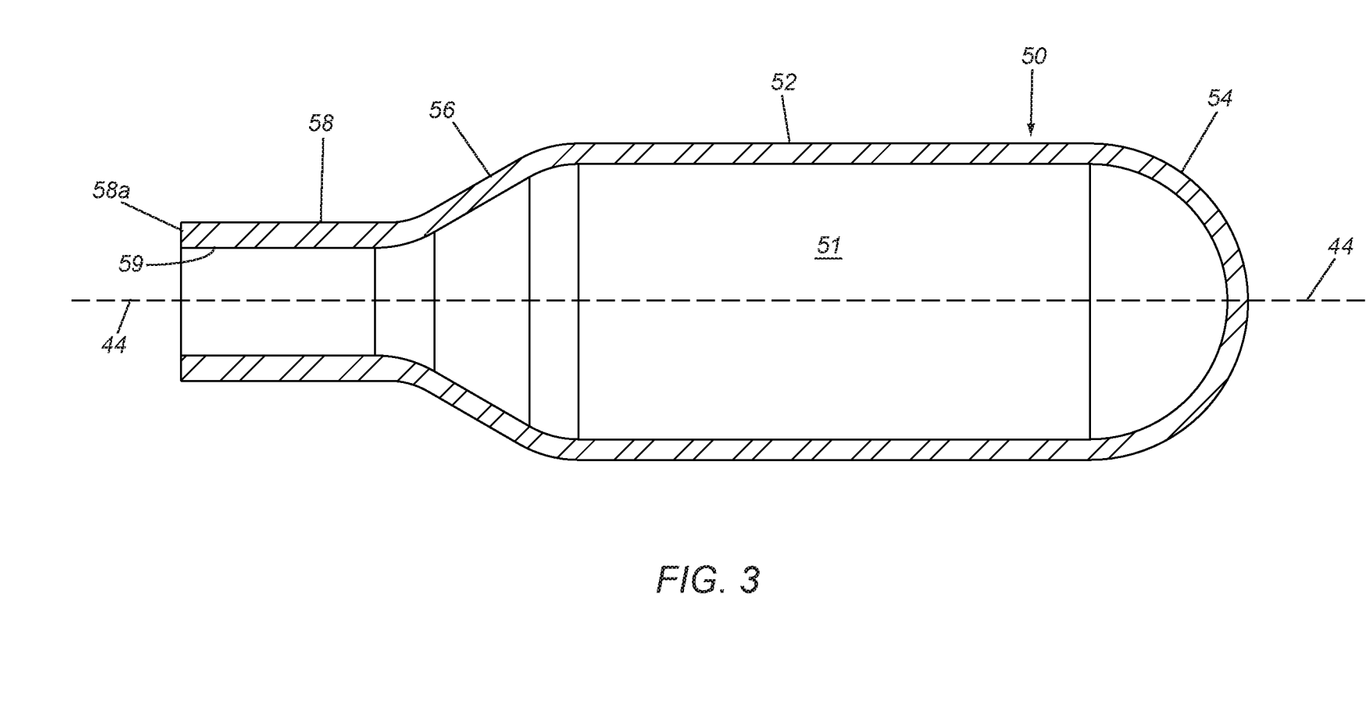
FIG. 3 is a cross-sectional detail of the body of the canister of FIG. 2.

In some embodiments, the body 50 and cap 60 are formed from stainless steel or other desired or suitable metal, or other material. In some embodiments, one or more of the body 50 and cap 60 may be formed by one or more of drawing, stamping, machining, casting, molding, and the like. For example, with reference to FIG. 3, the body 50 may be deep drawn from sheet metal, e.g., a round sheet metal blank of Type 305 stainless steel, using one or more dies and punches (not shown), e.g., to form a main barrel region 52 and enclosed base or first end 54 of the body 50. Additional processing may be used to form a tapered shoulder region 56 and open neck region or second end 58 defining an opening or passage 59 communicating with an interior 51 of the body 50. For example, the shoulder and neck regions 56, 58 may be formed by necking and the like, such that the neck region 58 has a substantially uniform diameter smaller than the diameter of the main barrel region 52. The regions of the body 50 may be substantially radially symmetrical about a central axis 44 of the canister 40. The neck region 58 may terminate in a substantially planar end wall 58a defining a plane substantially perpendicular to the axis 44.

In an exemplary embodiment, the body 50 may have a length between the first end 54 and the end wall 58a of the neck region 58 that is less than about thirty millimeters (30 mm), the outer diameter of the barrel region 52 may be not more than about ten millimeters (10 mm) or not more than about eight millimeters (8 mm), and the outer diameter of the neck region 58 may be not more than about five millimeters (5 mm), or not more than about four millimeters (4 mm). The neck region 58 may have a substantially uniform diameter length between about three to eight millimeters (3-8 mm) or between about four to six millimeters (4-6 mm), e.g., having sufficient length to accommodate the O-ring 36 and carriage 32 sliding along the neck region 58 during actuation of the IOL inserter 10, as described elsewhere herein. However, the provided dimensions and shapes are merely examples. Thus, the various dimensions of the various aspects of the canister 40 may be selected to be any desired dimension. Further, the shapes of the various aspects of the canister may be any desired shape. For example, one or more shapes of one or more aspects of the canister may be radially asymmetrical relative to the central axis 44 of the canister 40.

Figure 4A:
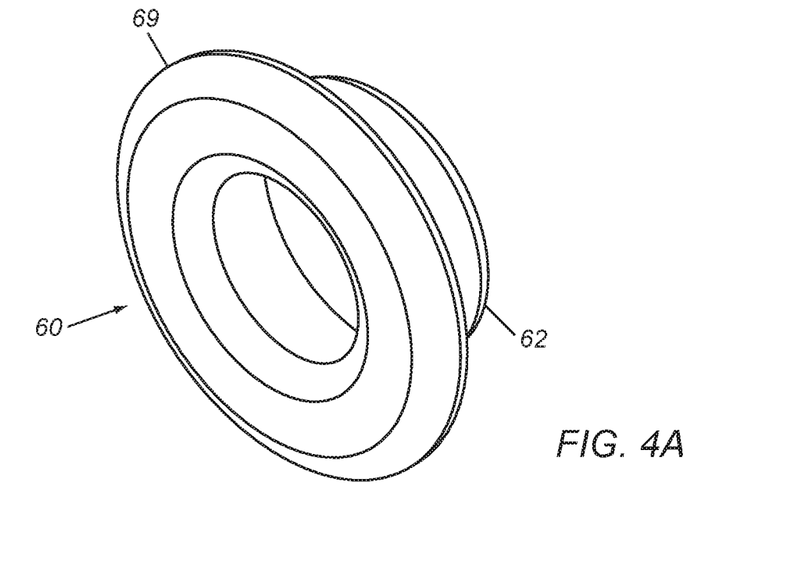
FIGS. 4A and 4B are perspective and cross-sectional views of the cap of the canister of FIG. 2.
Figure 4B:
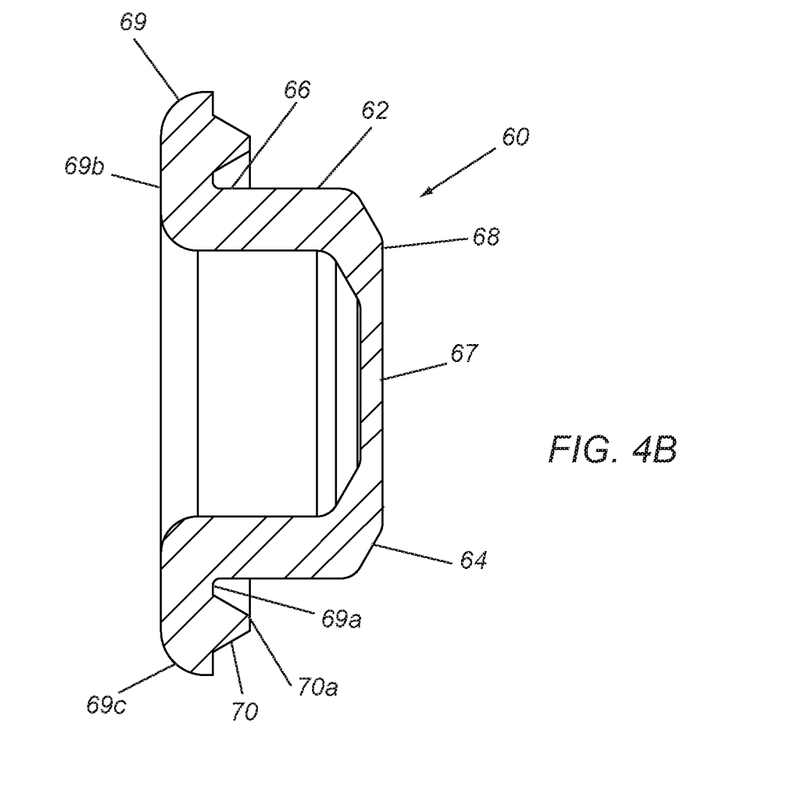

Similarly, as best seen in FIGS. 4A and 4B, the cap 60 may be drawn from another blank, e.g., to define an annular body 62 having a relatively thin closed or first end 64 and an open second end 66 also symmetrical about the axis 44. The annular body 62 may have an outer diameter smaller than the neck region 58 of the body 50 such that the annular body 62 may be inserted into the opening 59 while providing a desired clearance between the annular body 62 and the neck region 58, which facilitates projection welding the cap 60 to the body 50, as described elsewhere herein.

The closed end 64 is formed to include a penetrable wall or septum 67 having a desired diameter and/or thickness for accessing the gas within the cavity 42 once the canister 40 is loaded into a medical device, as described further elsewhere herein. In an exemplary embodiment, the septum 67 may have a substantially uniform thickness. For example, in some embodiments, the septum 67 may have a wall thickness between about 0.10-0.25 mm. In other embodiments, the septum 67 may have a wall thickness of not more than about 0.15 mm. In some embodiments, the septum 67 may have a diameter between about 0.80-1.20 mm. In other embodiments, the septum 67 may have a diameter of not more than about 1.0 mm. Although some example dimensions are provided, the scope of the disclosure is not so limited. Rather, the dimensions and shapes of various aspects of the cap 60 may be any desired shape or dimension. For example, the various dimensions and shapes of the cap 60 may be selected based on the application of the cap 60 and/or canister 40.

The septum 67 may be surrounded by thicker shoulder 68 to support the septum 67 while allowing the septum 67 to be penetrated during operation of a medical device. For example, in some embodiments, the septum 67 may be penetrated during loading of the canister 40 into a medical device. In other embodiments, the septum 67 may be penetrated some time after installation of the canister 40 into the medical device, such as, for example, during actuation of the medical device. For example, the septum 67 may be sized to engage the pin 34 of the IOL inserter 10 shown in FIG. 1B when the canister 40 is loaded into the chamber 16 of the IOL inserter 10 such that the pin 34 easily punctures the septum 67 with a desired maximum puncture force when the actuator 30 is first activated. In some embodiments, the force needed to puncture the septum 67 may be not more than about one hundred Newtons (100 N). In some embodiments, the force needed to puncture the septum 67 may be not more than about eighty Newtons (80 N). However, the force needed to puncture the septum 67 may be selected to be any desired force. Thus, in some embodiments, the puncture force may be greater than eighty Newtons (80 N) or greater than one hundred Newtons (100 N). Upon puncture of the septum 67, the gas within the canister 40 is controllably released during use of the IOL inserter 10, as described elsewhere herein.

The second end 66 of the cap 60 includes an annular flange 69 extending radially outwardly relative to the annular body 62, e.g., substantially perpendicular to the axis 44, thereby defining a lower surface 69a adjacent the annular body 62 and an upper surface 69b opposite the lower surface 69a. The lower surface 69a may be substantially planar and may include an annular projection 70 that is spaced apart from the annular body 62 and from an outer edge 69c of the annular flange 69. In some embodiments, the projection 70 may extend entirely around the annular body 62 along the lower surface 69a. In some embodiments, the projection 70 may be continuous. In other embodiments, the projection 70 may be discontinuous. In an exemplary embodiment, the projection 70 may taper from the lower surface 69a and terminate in a substantially planar end surface 70a, e.g., having a height between about 0.2-0.3 mm, e.g., about 0.25 mm.

Once formed, the body 50 and cap 60 may be further processed, e.g., deburred, have sharp edges broken, and the like, to provide, for example, a desired finish for the components before assembly.

The cap 60 may be substantially permanently attached to the body 50, e.g., by projection welding. For example, in an exemplary process, the body 50 and cap 60 may be placed in a filling chamber (not shown) and the filling chamber may be filled with carbon dioxide (or other gas) to a desired pressure, thereby filling the interior 51 of the body 50 with the $CO_2$. The filling chamber may be controlled to a desired temperature such that it is below the saturation temperature of the gas at filling pressure to condense the gas in the canister 40, thus filling the canister 40 with liquefied gas.

Once filled, the cap 60 may be welded to the neck region 58 to close the interior 51 and seal the liquid $CO_2$ within the resulting canister 40. For example, the first end 64 of the annular body 62 may inserted into the passage 59 in the neck region 58 such that the wall of the annular body 62 is spaced apart from the inner surface of the neck region 58, e.g., until the end surface 70a of the projection 70 contacts the end wall 58a of the neck region 58. In this manner, when the cap 60 is welded to the body 50, the resulting weld may be formed between the projection 70 and the end wall 58a of the neck region 58. For example, in an exemplary projection welding procedure, the body 50 may be coupled to ground within the filling chamber and an electrode may be placed against the upper surface 69b of the annular flange 69 on the cap 60, thereby holding the projection 70 against the end wall 58a of the neck region 58. Once the body 50 and cap 60 are engaged, electrical energy may be applied to the electrode, thereby forming a weld to attach the cap 60 and seal the resulting cavity 42 of the canister 40 with a desired volume of liquid CO2 therein.

When the canister 40 is removed from the filling chamber, the CO2 may return to its gaseous state or a mixed liquid-gaseous state, thereby providing a desired pressure within the cavity 42. In an exemplary embodiment, the mass of CO2 provided within the canister 40 after filling may be about six hundred milligrams (600 mg) or less, or about five hundred milligrams (500 mg) or less and/or having a resulting density between about 0.50-1.0 kg/L or between about 0.50-0.75 kg/L. In still other embodiments, the mass and/or density of the fluid, such as CO2, within the canister 40 may be selected to be any desired mass or density. Further, it will be appreciated that gases or fluids other than CO2 may be used to fill the canister 40 that provide a desired pressure and/or discharge force during use, as desired.

Figure 5A:
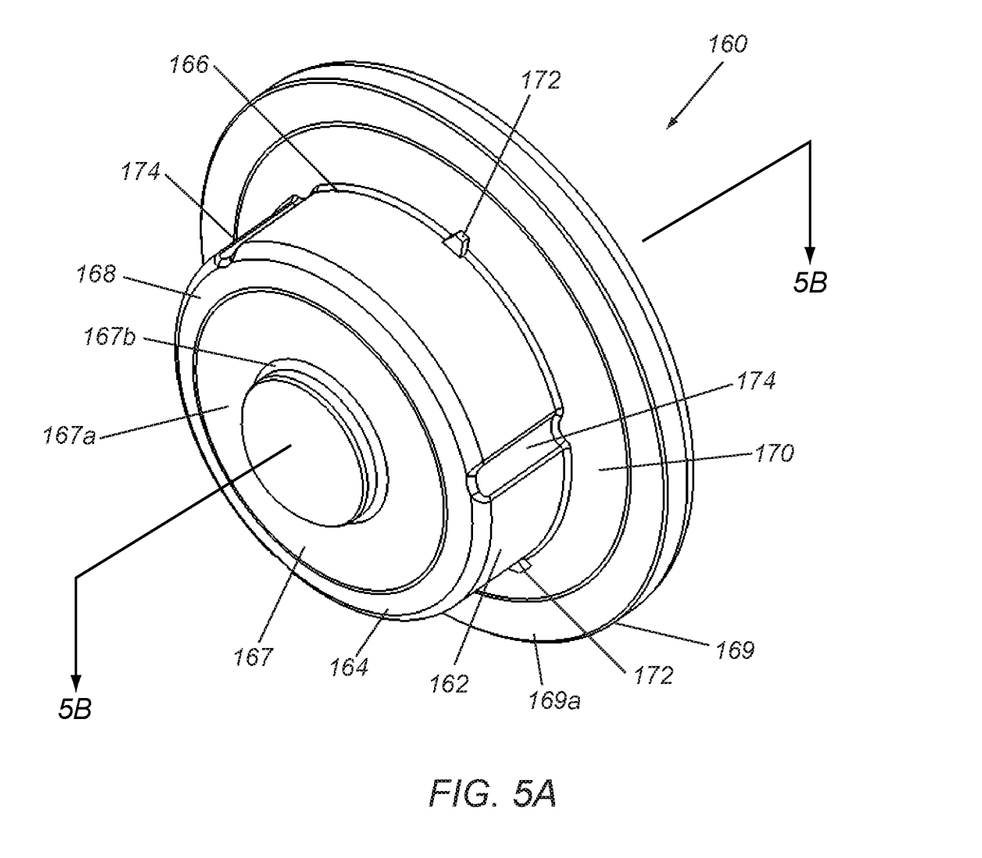
FIGS. 5A and 5B are perspective and cross-sectional views of another embodiment of a cap.
Figure 5B:
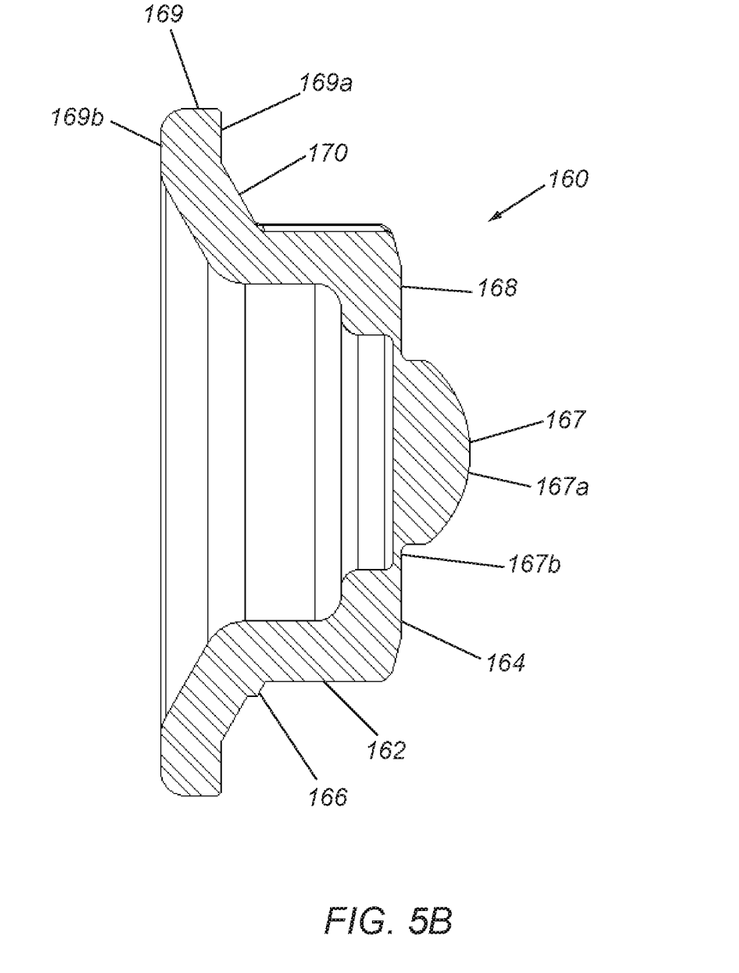

Turning to FIGS. 5A and 5B, another embodiment of a cap 160 is shown that may be formed using similar materials and methods as the cap 60, e.g., drawn from a blank to define an annular body 162 having a relatively thin closed or first end 164 and an open second end 166. The annular body 162 may have an outer diameter smaller than the neck region 58 of the body 50 such that the annular body 162 may be inserted into the opening 59 while providing a desired clearance between the annular body 162 and the neck region 58, which facilitates projection welding the cap 160 to the body 50, as described elsewhere herein.

Figure 6:
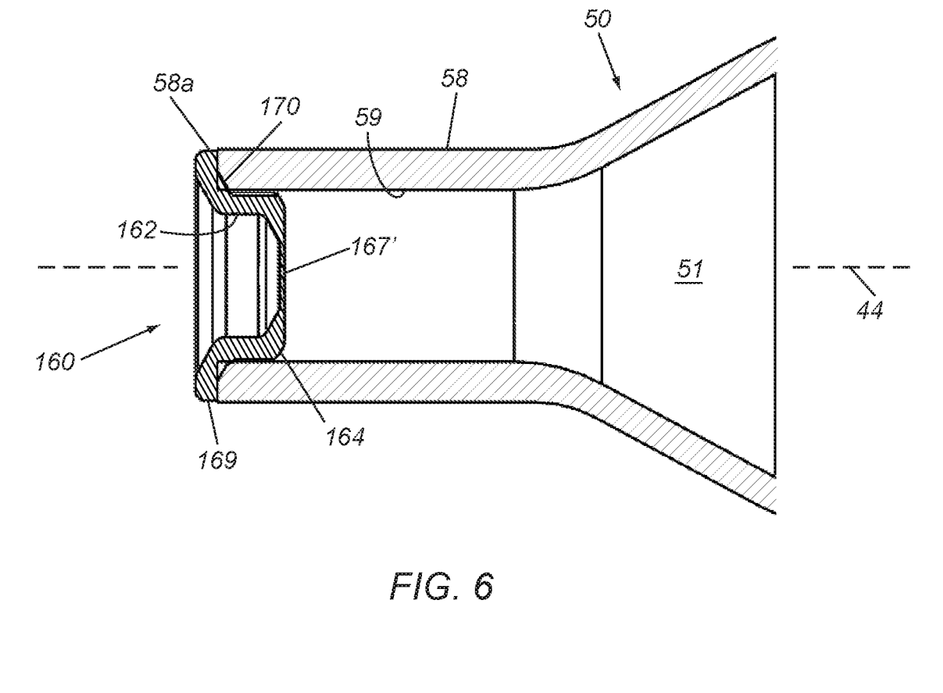
FIG. 6 is a cross-sectional detail showing the cap of FIGS. 5A and 5B being attached to the neck of a body, such as the body of FIG. 3.

The closed end 164 is formed to include a separable wall or septum 167 having a desired diameter and/or thickness for accessing the gas within the cavity 42 once the canister 40 is loaded into a medical device (not shown), as described further elsewhere herein. For example, as shown in FIGS. 5A and 5B, the septum 167 may include a relatively thicker central region 167a at least partially surrounded by a relatively thin perimeter 167b. Optionally, the perimeter 167b may completely surround the central region 167a or may extend only partially around the central region 167a, e.g., to provide a preferential hinge, as explained further elsewhere herein. Optionally, the central region 167a may have dome shape, e.g., as best seen in FIG. 5B or may have a substantially uniform thickness that is substantially thicker than the perimeter 167a. Alternatively, the cap 160 may include a relatively thin-walled septum 167' similar to the cap 60, e.g., as shown in FIG. 6, or the cap 60 shown in FIGS. 4A and 4B may include a thin perimeter surrounding a thicker central region (not shown).

The septum 167 may be surrounded by thicker shoulder 168 to support the septum 167 while allowing the septum 167 to be at least partially separated from the shoulder 168 during operation of a medical device. For example, in some embodiments, the septum 167 may be pressed inwardly to cause the perimeter 167b, e.g., by pin 34 as shown in FIG. 1C, to at tear or otherwise separate at least partially between the central region 167a and the shoulder during or after loading of the canister 40 into a medical device, as described elsewhere herein.

The second end 166 of the cap 160 includes an annular flange 169 extending radially outwardly relative to the annular body 162, e.g., substantially perpendicular to the axis 44, thereby defining a lower surface 169a adjacent the annular body 62 and an upper surface 169b opposite the lower surface 169a. The lower surface 169a may be substantially planar and may include an annular chamfer 170 that transitions from the lower surface 169a to the second end 166 of the annular body 162, e.g., to provide a welding interface for attaching the cap 160 to the body 50, as described further elsewhere herein.

Optionally, the annular body 162 may include one or more radial projections 172, e.g., a plurality of projections 172 spaced apart around the circumference of the second end 166. The projections 172 may be sized to contact the inner surface of the neck region 58 immediately adjacent the end wall 58a (shown in FIG. 6) to hold the cap 160 stationary and/or centered on the neck region 58 during attachment. In addition or alternatively, the annular body 162 may include one or more grooves or passages 174 in the outer surface of the annular body 162, e.g., a plurality of passages 174 extending between the first and second ends 164, 166, which may facilitate gas entering the interior of the canister 40 during filling.

For example, with additional reference to FIG. 6, the first end 164 164 of the cap 160 may be inserted into the passage 59 in the neck region 58 of the body 50 until the flange 169 contacts the end wall 58a of the neck region 58. The projections 172 (not shown in FIG. 6) may hold the cap 160 in place and/or center the cap 160 within the passage 59.

Similar to other methods herein, in an exemplary process, the body 50 and cap 160 may be placed in a filling chamber (not shown) and the filling chamber may be filled with carbon dioxide (or other gas) to a desired pressure, thereby filling the interior 51 of the body 50 with the CO2. The passages 174 may facilitate the gas passing by the cap 160 into the interior 51.

Once filled, the cap 160 may be welded to the neck region 58 to close the interior 51 and seal the liquid CO2 within the resulting canister 40. For example, the first end 164 of the annular body 162 may inserted into the passage 59 in the neck region 58 such that the wall of the annular body 162 is spaced apart from the inner surface of the neck region 58, e.g., until the lower surface 169a of the flange 169 contacts the end wall 58a of the neck region 58. Once the body 50 and cap 160 are engaged, electrical energy may be applied to the electrode, thereby forming a weld to attach the cap 160 and seal the resulting cavity 42 of the canister 40 with a desired volume of liquid CO2 therein. When the cap 160 is welded to the body 50, the chamfer 170 may localize the resulting weld to the inner perimeter of the neck region 58, provide line contact to localize weld current to enable a consistent weld, may center the cap 160 in the neck region 58, and/or reduce flaring of the outer neck diameter.

Optionally, after the canister 40 is removed from the filling chamber, the canister 40 may be weighed to confirm that a desired amount of gas has been loaded into the canister 40. For example, the mass and pressure of the gas may be determined by comparing the mass after filling with the original mass of the body 50 and cap 60, e.g., to confirm that the mass and pressure lie within desired tolerances. For example, it may be desirable to confirm that the pressure within the canister 40 does not exceed a desired maximum density (e.g., 0.75 mg/mL), which may otherwise result in the canister 40 exceeding regulatory standards and/or safe pressures. Again, the density and/or mass of the fluid contained within the canister 40 may be any desired density or mass.

During subsequent storage of the canister 40 (e.g., during its normal shelf life before being loaded into and used with a medical device), it may be desirable to weigh the canister 40 again, e.g., to ensure that the gas has not leaked from the canister 40. For example, despite the cap 60 being welded to the body 50, gas may still leak from the canister 40 and, therefore, the canister 40 may be weighed to ensure that an adequate fill of gas remains to ensure sufficient gas through the stroke of the medical device into which the canister 40 is to be loaded. One approach is to weigh the canister 40 following filling; expose the canister 40 to elevated temperatures to raise the internal pressure to accelerate any leakage that may be present; reweigh the canister 40 to determine if the mass has been reduced indicating the leak; and then extrapolate the leakage rate over the shelf life to ensure that sufficient gas will remain in the canister 40 over the shelf life of the product.

Forming the body 50 and cap 60 from stainless steel may provide corrosion protection for the resulting canister 40 over its target shelf life. Galvanized steel has been used for conventional gas canisters to provide corrosion protection, but may be inadequate for the canister 40. In particular, metallic plating, e.g., zinc, cannot be applied before welding the cap 60 to the body 50 since the plating would be lost at the weld, thereby compromising the corrosion protection. If additional plating were applied to the weld, the plating may not have a uniform thickness (on each canister and between different canisters). However, it will be appreciated that any appropriate and/or desired material, such as metal, plastic, and/or composite materials, may be used instead of stainless steel or galvanized steel.

Such variances in plating (before or after welding) may not meet the required tolerances to ensure that the mass and/or pressure of the gas within the finished cylinder falls within the desired range. Stainless steel can be formed to higher tolerances since no such plating is needed, thereby ensuring that the properties of the gas may be accurately determined after filling and/or over the shelf life of the canister.

Subsequently, during manufacturing, the canister 40 may be loaded into a medical device to provide an energy source that may be controllably released to provide a desired discharge force to operate the medical device. As explained above, in some embodiments, the energy source may be pressurized $CO_2$. For example, in some embodiments, the IOL inserter 10 may be provided to the user with the canister 40 pre-loaded within the chamber 16 of the housing 12. Thus, in some instances, a medical device pre-loaded with the canister 40 may be a disposable, single-use device. In some embodiments, the cap 14 may be substantially permanently coupled to the housing 12, e.g., by bonding with adhesive, sonic welding, interference fit, one or more connectors, and the like (not shown) to prevent the cap 14 and canister 40 from being removed by the user.

Alternatively, the IOL inserter 10 may be a reusable device, e.g., in which the user may load one or more canisters 40 successively into the housing 12, as desired. For example, with the IOL inserter 10 shown in FIGS. 1A and 1B, the user may remove the cap 14 and load a canister 40 into the chamber 16 of the main body portion 12 of the IOL inserter 10, e.g., such that the septum 67 of the cap 60 is disposed adjacent the pin 34, as shown in FIG. 1A. The cap 14 may then be reconnected to the main body portion 12 to secure the canister 40 within the housing 12.

At any time, the actuator 30 may be activated to direct the carriage 32 proximally to the proximal position shown in FIG. 1B such that the pin 34 penetrates the septum 67, thereby delivering $CO_2$ from the canister 40 into one or more passages of the IOL inserter 10. Alternatively, in the embodiment shown in FIGS. 5A and 5B, the perimeter 167b of the septum 167 may tear or otherwise separate at least partially around the central region 167a, thereby delivering $CO_2$ from the canister 140. The released $CO_2$ may be used to pressurize an incompressible liquid, e.g., silicone oil, within the housing 12. The pressurized incompressible liquid may be used to deliver a lens from the lens compartment 22. The O-ring seal 36 may slide along the neck region 58 and prevent $CO_2$ from leaking into the chamber 16 or elsewhere other than the intended passages within the IOL inserter 10. The actuator 30 may then be released, allowing the carriage 32 to return to the distal position shown in FIG. 1A.

In embodiments in which the lens compartment 22 defines a separate lens cartridge, the lens compartment 22 may loaded into the lens delivery portion 20 (or may already be loaded). However, as explained above, the lens compartment 22 may be fixedly attached to the main body portion 12 or form an integral portion thereof. The actuator 30 of the IOL inserter 10 may be activated at any time to controllably deliver the incompressible fluid under constant pressure from the $CO_2$, e.g., silicone oil, to deliver the lens from the lens compartment 22. For example, the actuator 30 may be selectively actuated such that the flow rate of the incompressible liquid is proportional to the extent the actuator 30 is activated, e.g., to advance the lens from the lens compartment 22 at a controlled speed, e.g., as described in the applications incorporated by reference herein.

After the procedure, the entire IOL inserter 10 may be disposed of or, if reusable, the canister 40 may be removed, the medical device may be cleaned and/or otherwise prepared for another procedure, at which time another canister may be loaded into the medical device.

Although the gas canisters herein have been described for use with an IOL inserter, it will be appreciated that the gas canisters may be used with other medical devices. For example, the gas canisters may be used within a syringe device, such as that disclosed in U.S. Patent Application Publication No. 2013/0317478, the entire disclosure of which is expressly incorporated by reference herein. For example, such a syringe device may include a needle or other cannula that may be used to deliver viscous or other fluids contained within the device into an eye, with the gas canister providing a discharge force that may be controlled by an actuator of the syringe device to controllably deliver the fluid into an eye. In another embodiment, the gas canisters may be used to deliver a tubular shunt or other implant (not shown) into an eye or other region of a patient's body.

It is fully contemplated that the features, components, and/or steps described with respect to one or more embodiments, methods, or Figures may be combined with the features, components, and/or steps described with respect to other embodiments, methods, or Figures of the present disclosure.

While the various examples described herein are susceptible to various modifications, and alternative forms, specific examples thereof have been shown in the drawings and are herein described in detail. It should be understood that the scope of the present disclosure is not to be limited to the particular forms or methods disclosed, but to the contrary, the scope of the disclosure is intended to cover all modifications, equivalents and alternatives falling within the scope of the appended claims.

We claim:

1. A canister, comprising:
   a cylindrical body comprising a barrel region defining a
     first diameter, an enclosed first end, and a neck region defining a second diameter smaller than the first diameter and extending from the barrel region to an open second end defining an end wall, the cylindrical body defining a central axis extending between the first end and the second end; and a cap comprising an annular portion including a closed first end and an open second end opposite the first end, a separable septum formed in the first end of the cap, and an annular flange extending radially from the second end of the annular portion of the cap, the flange including a lower surface defining a plane substantially perpendicular to the central axis, the septum formed in the first end comprising a central region, a perimeter region at least partially surrounding the central region, and an annular shoulder surrounding the perimeter region and extending inwardly from the annular portion, the perimeter region having a thickness thinner than the thickness of the central region and the annular shoulder for preferentially tearing of the perimeter region to at least partially separate the central region from the annular shoulder, the first end of the annular portion of the cap inserted into the open second end of the cylindrical body such that the annular portion is spaced from an interior surface of the neck region and the septum is disposed within the neck region, the lower surface of the annular flange secured to the end wall of the second end of the cylindrical body, thereby enclosing a cavity, the cavity filled with pressurized gas.

2. The canister of claim 1, wherein the cylindrical body and cap are formed from stainless steel.

3. The canister of claim 2, wherein the second diameter of the neck region is not more than about five millimeters (5 mm).

4. The canister of claim 2, wherein the second diameter of the neck region is not more than about four millimeters (4 mm).

5. The canister of claim 1, wherein the septum has a thickness between about 0.10-0.25 mm.

6. The canister of claim 1, wherein the septum has a thickness of not more than about 0.15 mm.

7. The canister of claim 1, wherein the cylindrical body has a length between the first end and the end wall of the second end that is less than about thirty millimeters (30 mm).

8. The canister of claim 1, wherein the first diameter of the barrel region is not more than about ten millimeters (10 mm).

9. The canister of claim 1, wherein the first diameter of the barrel region is not more than about eight millimeters (8 mm).

10. The canister of claim 1, wherein the septum has a diameter between about 0.80-1.20 mm.

11. The canister of claim 1, wherein the septum has a diameter of not more than about 1.0 mm.

12. The canister of claim 1, wherein the annular portion further comprises one or more axial passages in an outer surface extending between the first and second ends to provide a path for gas to enter the interior during filling.

13. A canister, comprising:

a cylindrical body comprising a barrel region defining a first diameter, an enclosed first end, and a neck region defining a second diameter smaller than the first diameter and extending from the barrel region to an open second end defining an end wall, the cylindrical body defining a central axis extending between the first end and the second end; and a cap comprising an annular portion including a closed first end and an open second end opposite the first end, a separable septum formed in the first end of the cap, and an annular flange extending radially from the second end of the annular portion of the cap, the flange including a lower surface defining a plane substantially perpendicular to the central axis, the first end of the annular portion of the cap inserted into the open second end of the cylindrical body such that the annular portion is spaced from an interior surface of the neck region and the septum is disposed within the neck region, the lower surface of the annular flange secured to the end wall of the second end of the cylindrical body, thereby enclosing a cavity, the cavity filled with pressurized gas, wherein the septum is formed in the first end and comprising a central region, a perimeter region at least partially surrounding the central region, and an annular shoulder surrounding the perimeter region and extending inwardly from the annular portion, the perimeter having a thickness thinner than the thickness of the central region and the annular shoulder for preferentially tearing of the perimeter to at least partially separate the central region from the cap.

14. The canister of claim 13, wherein the perimeter completely surrounds the central region.

15. The canister of claim 13, wherein the perimeter extends partially around the central region to define a preferential hinge.

16. The canister of claim 13, wherein the central region has a dome shape.

* * * * *